US007829193B2

(12) United States Patent
Lorentz et al.

(10) Patent No.: US 7,829,193 B2
(45) Date of Patent: Nov. 9, 2010

(54) COATING COMPOSITIONS COMPRISING AN AQUEOUS DISPERSION OF FILM-FORMING POLYMER AND A SILICONE POLYETHER, PROCESS FOR THE PREPARATION THEREOF AND USES THEREOF, IN PARTICULAR AS AN ANTISOILING COATING

(75) Inventors: Gilles Lorentz, Lyons (FR); Daniel Joubert, Vineuil Saint Firmin (FR)

(73) Assignee: Hexion Specialty Chemicals, Inc., Columbus, OH (US)

( * ) Notice: Subject to any disclaimer, the term of this patent is extended or adjusted under 35 U.S.C. 154(b) by 722 days.

(21) Appl. No.: 10/574,413

(22) PCT Filed: Oct. 8, 2004

(86) PCT No.: PCT/FR2004/002553

§ 371 (c)(1),
(2), (4) Date: Sep. 17, 2007

(87) PCT Pub. No.: WO2005/035675

PCT Pub. Date: Apr. 21, 2005

(65) Prior Publication Data

US 2008/0090089 A1 Apr. 17, 2008

(30) Foreign Application Priority Data

Oct. 8, 2003 (FR) .................................. 03 11759

(51) Int. Cl.
*B32B 27/30* (2006.01)

(52) U.S. Cl. ....................................... 428/447; 525/474
(58) Field of Classification Search ................. 428/447; 525/474

See application file for complete search history.

(56) References Cited

U.S. PATENT DOCUMENTS

| 3,337,351 A | 8/1967 | Morehouse |
| 3,933,407 A | 1/1976 | Tu et al. |
| 6,552,212 B2 * | 4/2003 | Walele et al. ............... 556/437 |
| 2005/0014886 A1 * | 1/2005 | Yanutola et al. ............ 524/503 |

FOREIGN PATENT DOCUMENTS

| DE | 10156078 | 6/2003 |
| EP | 0679699 | 11/1995 |
| GB | 1521156 | 8/1978 |
| JP | 04370176 | 12/1992 |
| JP | 2003119397 | 4/2003 |

OTHER PUBLICATIONS

Silwet Surfactants—Momentive Performance Materials (2008).*

* cited by examiner

*Primary Examiner*—Kuo-Liang Peng

(57) ABSTRACT

The present invention relates to novel coating compositions, or surface-treatment compositions, in particular paint compositions. These compositions can be used in various applications, such as interior or exterior water-based paints, render, varnish, a semi-thick coating, formulations for finishes for architectural textiles, rigid or flexible plastic surfaces, or surface-protection products.

19 Claims, 1 Drawing Sheet

DEPOSITION OF THE DIRTY OIL SOILING ON TREATED TEST PIECES

AFTER PASSAGE UNDER A STREAM OF WATER

COATING COMPOSITIONS COMPRISING AN AQUEOUS DISPERSION OF FILM-FORMING POLYMER AND A SILICONE POLYETHER, PROCESS FOR THE PREPARATION THEREOF AND USES THEREOF, IN PARTICULAR AS AN ANTISOILING COATING

The present invention relates to novel coating compositions, or surface-treatment compositions, in particular paint compositions. These compositions can be used in various applications, such as interior or exterior water-based paints, render, varnish, a semi-thick coating, formulations for finishes for architectural textiles, rigid or flexible plastic surfaces, or surface protection products. They are advantageously used to produce antisoiling coatings.

The prior art does not indicate any coating composition able to correctly form a film, which confers on the final application, for example in the form of paint, a strong hydrophilicity at the exterior surface of the coating, which is long-lasting, i.e. which withstands washing, without reducing the ability of the coating to protect, i.e. without deteriorating the formation of the protective film or the adhesion thereof to the support that is coated.

One of the essential objectives of the present invention is therefore to provide a novel coating composition that confers on the final application a strong hydrophilicity at the exterior surface of the coating, which is long-lasting, i.e. withstands washing, without reducing the ability of the coating to protect, i.e. without deteriorating the formation of the protective film or the adhesion thereof to the support that is coated.

DESCRIPTION OF THE FIGURES

The following is a brief description of figures wherein like numbering indicates like elements as necessary.

Figure 1:
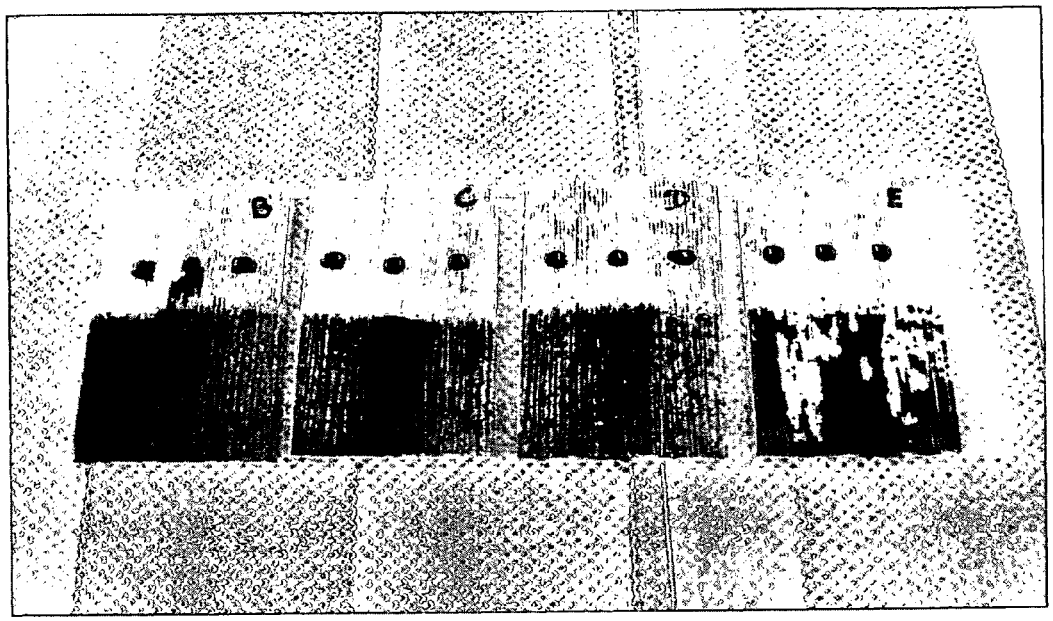
FIG. 1 are pictures showing at top, deposition of dirty oil soiling on treated test pieces, and at bottom, the substrates after exposure to a water stream.
Figure 1:
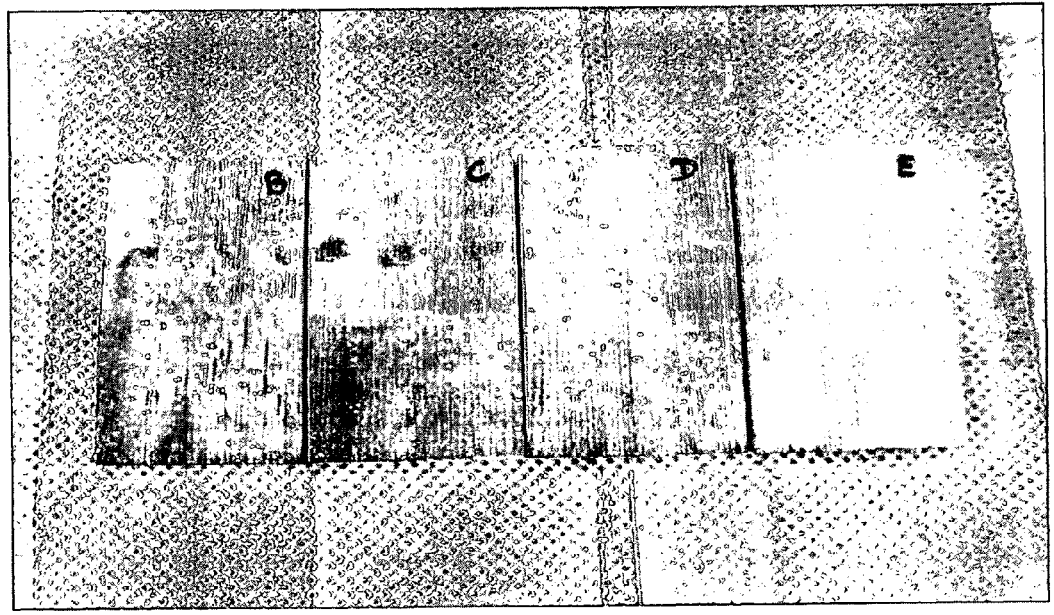

More concretely, the novel coating composition, developed and forming the subject of the present invention, comprises:
an aqueous dispersion of film-forming polymer, and
a sufficient amount of a silicone polyether satisfying formula (I) below:

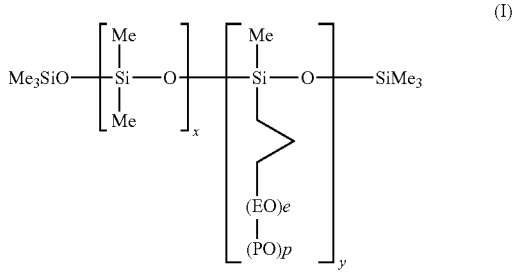

(I)

the terminal groups of the ethylene oxide or propylene oxide being OR groups in which:
EO signifies —O—$CH_2$—$CH_2$—
PO signifies —O—$CH_2$—$CH_2$—$CH_2$—
R represents a hydrogen atom, or a linear or branched alkyl radical having from 1 to 22 carbon atoms, and preferably having from 1 to 4 carbon atoms,
x is a number between 5 and 50,
y is a number between 3 and 10,
e is a number between 10 and 30,
p is a number between 0 and 10,
it being understood that:
x/y is less than 10, and preferably less than or equal to 8,
e+p is less than 30, and preferably less than or equal to 20,
e/p is greater than 1, and preferably greater than or equal to 4, and
x+y is less than 60, and preferably less than 40.

The preferred forms are particularly the products for which x=9.5, y=3.5, e=11.5 and p=2.5, and R is a hydrogen atom; x=14, y=4, e=17 and p=1, and R is a hydrogen atom; x=48, y=6, e=15 and p=5, and R is a hydrogen atom.

These products are all nonaqueous liquid products.

The expression "aqueous dispersion of water-insoluble film-forming polymer (latex)" is intended to mean natural or synthetic latices.

The preferred water-insoluble film-forming polymers are obtained by polymerization of monomers chosen from:
vinyl esters, and more particularly vinyl acetate;
alkyl acrylates and methacrylates in which the alkyl group contains from 1 to 10 carbon atoms, for example methyl acrylates and methacrylates, ethyl acrylates and methacrylates, n-butyl acrylates and methacrylates, and 2-ethylhexyl acrylates and methacrylates;
vinylaromatic monomers, in particular styrene.

These monomers can be copolymerized with one another or with other ethylenically unsaturated monomers, so as to form homopolymers, copolymers or terpolymers.

By way of nonlimiting examples of monomers copolymerizable with vinyl acetate and/or acrylic esters and/or styrene, mention may be made of ethylene and olefins such as isobutene; vinyl esters of branched or unbranched, saturated monocarboxylic acids having from 1 to 12 carbon atoms, such as vinyl propionate, vinyl "Versatate" (registered trade mark for esters of $C_9$-$C_{11}$ branched acids), vinyl pivalate, vinyl laurate; esters of unsaturated mono- or dicarboxylic acids having 3 to 6 carbon atoms with alkanols having 1 to 10 carbon atoms, such as methyl, ethyl, butyl or ethylhexyl maleates, or methyl, ethyl, butyl or ethylhexyl fumarates; vinylaromatic monomers such as methylstyrenes or vinyltoluenes; vinyl halides such as vinyl chloride, vinylidene chloride, diolefins, particularly butadiene; (meth)acrylic acid (meth)allyl esters, (meth)allyl esters of maleic acid mono- and diesters, fumaric acid mono- and diesters and itaconic acid mono- and diesters, and also alkene derivatives of acrylic and methacrylic acid amides, such as N-methallylmaleimide.

At least 2 copolymerizable monomers that are different in nature can in particular be chosen so as to obtain a terpolymer.

By way of example, mention may be made of a terpolymer of acetate/versatate/dibutyl maleate type.

The polymerization of the latex is carried out in a manner known in itself, as an aqueous emulsion of the polymerizable monomers in the presence of at least one free-radical initiator, and preferably of a transfer agent, for example of the mercaptan type, with a monomer concentration in the reaction medium of generally between 20 and 60% by weight.

The polymerization can be carried out continuously, batchwise or semi-continuously, with part of the monomers being introduced continuously, and can be of the "seeded" or "incremental" type according to any known variant for obtaining particles of homogeneous and heterogeneous structure.

For the preparation of latex, by way of nonlimiting example, reference will be made to the procedures described in patent EP 599 676 in the present applicant's name.

Preferably, use is made of acrylic coating compositions, i.e. they comprise polymers based on monomers of acrylic type (such as alkyl acrylates and methacrylates in which the alkyl group contains from 1 to 10 carbon atoms, for example methyl, ethyl, n-butyl or 2-ethylhexyl acrylates and methacrylates). They can also comprise other monomers; they may, for example, be a styrene-acrylic varnish.

However, in the applications intended, "pure" acrylic coating compositions, i.e. based on monomers of acrylic type only, are even more preferred.

The latices used are chosen such that their glass transition temperature (TG) is between 10 and 60° C., and preferably between 20 and 40° C.

The sizes of the polymer particles as an aqueous dispersion constituting the latices according to the invention can be between 300 manometers and 20 manometers. These particle sizes are measured by means of a laser granulometer or by scanning microscopy after freeze-fracture of the sample.

Optionally, the aqueous dispersions of film-forming polymers can comprise plasticizers, in order to decrease the film formation temperature (MFFT) when the process of the invention is used under very cold temperature conditions, i.e. at temperatures below 0° C.

In general, the sufficient amount of silicone polyether of formula (I) added to the aqueous dispersion of film-forming polymer (latex) is between 0.1 and 10% by weight of dry silicone polyether of formula (I) relative to the weight of dry latex.

Preferably, the sufficient amount of silicone polyether of formula (I) added to the aqueous dispersion of film-forming polymer (latex) is between 1 and 5% by weight of dry silicone polyether of formula (I) relative to the weight of dry latex.

The addition of silicone polyether of formula (I) must, of course, be suitably metered for economical and also technical reasons.

The addition of the silicone polyether of formula (I) is carried out by simple addition of the liquid silicone polyether to the aqueous dispersion of film-forming polymer (latex), i.e. by a liquid/liquid mixing technique.

The mixing of the silicone polyether of formula (I) and of the aqueous dispersion of film-forming polymer can be carried out by liquid/liquid mixing in any liquid/liquid mixer for mixing without causing the introduction of air.

The use of a silicone polyether of formula (I) of the invention in coating compositions has several advantages.

First of all, this compound is miscible, compatible and stable when it is mixed with the aqueous dispersion of film-forming polymer (latex).

Furthermore, it has the advantage of neither preventing nor modifying the film formation when the coating composition is applied to a support.

More particularly, this compound confers a strong hydrophilicity at the surface of the film formed, without reducing the ability of the coating to protect. Without wishing to be limited to a scientific theory or to a mechanism, it appears that this property is due to the fact that the silicone polyether, which carries hydrophilizing groups, is located, after formation of the film, only at the outermost surface of said film, on the side exposed to the air.

Furthermore, this compound confers this hydrophilicity effect on the coating in a long-lasting manner, and is not washed away by rain or washing.

The mixtures of latex and silicone polyether of formula (I) according to the invention are stable and remain homogeneous even after prolonged storage, and including when they are exposed to a temperature of 40° C. for 2 months.

The hydrophilicity conferred on the outermost surface by the addition of silicone polyethers of formula (I) is evaluated by the conventional "wetting angle" method. A drop of distilled water of calibrated size is deposited, under standardized and repetitive conditions, onto the surface to be studied. It spreads or shrinks to a greater or lesser degree according to the hydrophilicity of the surface, and with appropriate equipment, for instance a goniometer for measuring the wetting angle, for example a Tantec goniometer, it is possible to measure the angle formed by the drop deposited on the surface.

High contact angles greater than 70° correspond to hydrophobic surfaces. Small angles, in particular those less than 40° (which signifies that spreading of the water drop is obtained) correspond to hydrophilic surfaces.

The durability of the surface hydrophilicity conferred by the system according to the invention is evaluated by the same technique, but carried out on films or objects coated with these films which have been completely immersed in pure water for several periods of 12 hours, and then dried at 50° C. for 1 hour.

In the examples according to the invention, the surface hydrophilicity is always observed even after 15 cycles of complete immersion and drying.

Besides the two main constituents of the coating composition of the invention, the latter can also contain other additives, such as, for example, one or more antifoam(s), biocide(s), surfactant(s), rheological agent(s), coalescence agent(s), dispersant(s), and thickener(s).

However, preferably, the composition used is simply the combination between a latex and a silicone polyether according to the invention, of formula (I), and it is used as a finishing layer, over the conventional coating layer.

For the preparation of the coating composition, the various constituents are mixed in a manner known in itself.

The coating composition according to the invention can be applied according to the usual techniques. By way of example, it can be applied to the surfaces by any suitable means, such as paint brush, brush, spraying device, etc.

The surfaces to which the coating composition according to the invention can be applied are diverse in nature.

However, in order to obtain good hydrophilicity at the exterior surface of the coating, it is important to apply the coating composition to a hydrophobic support.

The hydrophobic supports are chosen from glass, metals, rigid polypropylene or polypropylene in the form of a nonwoven netting, wood treated with a first layer of latex according to the invention but without silicone polyether, or a cement-based material also treated with a first layer of latex also alone. They are therefore hydrophobic in the sense that the contact angle test with a drop of water gives wetting angles of the order of 70° or above.

It is therefore important to note that any support, including nonhydrophobic supports, can be rendered hydrophobic for the purposes of the present invention by prior coating with an adhesion primer, i.e. a composition of film-forming polymer as an aqueous dispersion (latex) or that is solvent-based.

For example, porous materials that are hydrophilic in nature, such as crude wood, cement, prefabricated objects made of cement or fibro cement, or else brick or unvarnished tiles, or textile sheets made of taut cotton, must be coated with a composition of film-forming polymer as an aqueous dispersion or that is solvent-based (hydrophobic adhesion primer) before the application of the coating composition according to the invention.

This hydrophobic adhesion primer can in particular be based on the latex which is used in the coating composition which is subsequently applied.

A subject of the invention is also a process for rendering a hydrophobic support more hydrophilic (wetting angle with water of the order of 30°) in a long-lasting manner, characterized in that a sufficient amount of a coating composition according to the invention is applied to the surface of the hydrophobic support.

A subject of the present invention is also a hydrophobic support whose surface is coated at least in part with a film resulting from the drying of a composition comprising an aqueous emulsion of film-forming polymer and at least one silicone polyether of formula (I).

The compositions of the invention are useful for various applications.

Preferably, the coating composition of the invention is used to produce an antisoiling coating.

Thus, a superhydrophilicity at the outermost surface of the coating, the latter being itself closed (nonporous) and hydrophobic in its mass, makes it possible to prevent the attachment of soiling or microorganisms. The superhydrophilicity at the outermost surface of the coating allows better washability of the surface with rainwater or simple hosing.

The coating composition according to the invention can therefore be used in a varnish or an exterior paint, but also an interior paint.

In fact, the problem of soiling exists for all elements exposed to the exterior, such as façades, "architectural" textiles (tarpaulin sheets, taut canvases, fixed canopies), painted metal surfaces, or wood, but also for interior elements, washable interior paints for a kitchen or bathroom, finishing varnishes of wallpapers, varnished tiled surfaces, wood, or prefabricated elements made of cement or fibro cements, for example.

The soiling may be fatty and carbon-based soiling, derived essentially from automobile pollution or urban heating systems. In this case, the soiling involves oils, soot, mixtures of oil and of carbon black particles, and smoke and soot aerosols.

However, the soiling may be soiling of biological origin consisting of lichens, and of algal and fungal symbioses.

By way of example, mention may also be made of the use of a coating composition of the invention for producing a more hydrophilic coating of the polymers used in nappies for babies.

The following examples and tests are given by way of illustration. They make it possible in particular to understand the invention more clearly and to reveal its advantages and show some variants of implementation.

Example 1

1—Compositions are prepared by addition of the candidate silicone polyethers to the latex, at ambient temperature, at a content of 3%, expressed on a dry/dry basis relative to the latex. Table I below gives the compositions of the products tested, according to formula (I) given above.

Two Rhodorsil products appear in this table and are commercial products sold by the company Rhodia.

The other products are products obtained on the laboratory scale.

The latex that is the subject of the trials is Rhodopas D2040, an acrylic latex sold by the company Rhodia.

2—The effects on the emulsion and on the stability over time are observed.

3—For the stable mixtures, a "film" 2 mm thick is prepared in a silicone impression. This makes it possible to extract the film easily and to carry out various tests or measurements on this film.

4—The hydrophilicity of the two faces (that having been exposed to the air and that not having been exposed) is measured by measuring the wetting angle of a drop of deionized water deposited at the surface, as specified above.

Table I below gives the definition of the silicone polyethers that are subjects of the trials.

TABLE I

|  | Product reference | Origin | x | y | e | p | R |
|---|---|---|---|---|---|---|---|
| Comparative example | Silicone polyether 1 | Rhodorsil SP3300 | 75 | 7 | 22 | 22 | H |
| Comparative example | Silicone polyether 2 | Laboratory product | 31 | 6 | 29 | 48 | H |
| Comparative example | Silicone polyether 3 | Laboratory product | 29 | 4.5 | 5.7 | 32.6 | H |
| Example of the invention | Silicone polyether 4 | Laboratory product | 14 | 4 | 17 | 1 | H |
| Example of the invention | Silicone polyether 5 | Laboratory product | 20 | 4 | 22 | 7 | H |
| Example of the invention | Silicone polyether 6 | Laboratory product | 19 | 5 | 25 | 4 | H |
| Example of the invention | Silicone polyether 7 | Laboratory product | 21 | 4 | 20 | 5 | H |
| Example of the invention | Silicone polyether 8 | Laboratory product | 9 | 3.5 | 12.3 | 0.6 | H |
| Example of the invention | Silicone polyether 9 | Laboratory product | 48 | 6 | 15 | 5 | H |
| Example of the invention | Silicone polyether 10 | Rhodorsil SP3301 | 9.5 | 3.5 | 11.5 | 2.5 | H |

Table II below gives the results of the hydrophilicity measurements on the films obtained from the latex+silicone polyether mixtures using the contact angle measuring technique.

TABLE II

|  | Reference of the latex + silicone polyether systems | Upper surface wetting angle | Lower surface wetting angle | Test result |
|---|---|---|---|---|
| Control | Rhodopas D2040 alone | 89° | 90° |  |
| Comparative example | Rhodopas D2040 + 3% SP1 | 55° | 85° | Negative |
| Comparative example | Rhodopas D2040 + 3% SP2 | 90° | 90° | Negative |
| Comparative example | Rhodopas D2040 + 3% SP3 | No film obtained |  | Negative |
| Example of the invention | Rhodopas D2040 + 3% SP4 | 27° | 89° | Positive |
| Example of the invention | Rhodopas D2040 + 3% SP5 | 27° | 90° | Positive |
| Example of the invention | Rhodopas D2040 + 3% SP6 | 26° | 88° | Positive |
| Example of the invention | Rhodopas D2040 + 3% SP7 | 25° | 87° | Positive |
| Example of the invention | Rhodopas D2040 + 3% SP8 | 26° | 88° | Positive |
| Example of the invention | Rhodopas D2040 + 3% SP9 | 26° | 90° | Positive |
| Example of the invention | Rhodopas D2040 + 3% SP10 | 25° | 87° | Positive |

These results make it possible to clearly select the silicone polyethers that make it possible to obtain the hydrophilicity of the upper face of the film.

Example 2

Durability of the Effect Obtained

As described above, the films that gave a positive result in the above example are immersed and dried 6 times over a period of one week, and the contact angle is then again measured on the lower and upper parts of the film. The results are given in Table III below:

TABLE III

| Reference of the latex + silicone polyether systems | Upper surface wetting angle | Lower surface wetting angle | Upper surface wetting angle after immersion test | Lower surface wetting angle after immersion test |
|---|---|---|---|---|
| Rhodopas D2040 + 3% SP4 | 27° | 89° | 28° | 88° |
| Rhodopas D2040 + 3% SP5 | 27° | 90° | 27° | 90° |
| Rhodopas D2040 + 3% SP6 | 26° | 88° | 26° | 88° |
| Rhodopas D2040 + 3% SP7 | 25° | 87° | 27° | 87° |
| Rhodopas D2040 + 3% SP8 | 26° | 88° | 26° | 88° |
| Rhodopas D2040 + 3% SP9 | 26° | 90° | 27° | 87° |
| Rhodopas D2040 + 3% SP10 | 25° | 87° | 27° | 87° |

It is noted that the hydrophilicity of the upper surface is completely conserved after the cycles of soaking and re-drying. It is therefore long-lasting and withstands repeated washing.

Example 3

Study of the Influence of the Dosage of Latex/Silicone Polyether According to the Invention Example 1 was carried out with silicone polyether contents of 3%.

Supplementary trials involved the addition of contents of 1%, 3%, 5% and 6% of the silicone polyether Rhodorsil SP3301 according to the invention to the latex Rhodopas D 2040, which are two products sold by Rhodia.

Measurement of the contact angles with the distilled water on the upper part of the film shows that a certain hydrophilicity is attained starting from an addition of 1%, and that it increases (decrease in the water-surface contact angle) with the content of silicone polyether added:

| No addition | 80° |
|---|---|
| 1% | 50° |
| 3% | 30° |
| 5% | 30° |
| 6% | 23° |
| 8% | 20° |

Beyond an addition of 8%, the hydrophilicity no longer increases.

Example 4

Hydrophilization of Certain Surfaces: in the Case of a Rigid Polypropylene Surface Most materials can be surface-hydrophilized using this system, on condition that the film adheres sufficiently to the surface in question.

In particular, we were able to render a rigid polypropylene surface hydrophilic by direct application (with a paint brush or by spraying) of a mixture of Rhodopas D 2040 latex and 5% of silicone polyether Rhodorsil SP3301.

TABLE IV

| Trials | Contact angle |
|---|---|
| reference polypropylene alone | 87° |
| polypropylene treated with latex + silicone Rhodorsil SP3301 using a paint brush | 30° |
| reference polypropylene | 90° |
| polypropylene treated with latex + silicone Rhodorsil SP3301 by spraying | 35° |

Example 5

Antisoiling Effect. Improved "Washability"

We sought to verify whether rendering a surface hydrophilic makes it possible to obtain better washability of this surface. This fact is established in the field of detergent formulations for washing laundry, which contain "antisoiling"

amphiphilic polymers whose function is to render synthetic textiles, in particular polyesters, hydrophilic on washing.

The material treated is planed solid wood, on which are deposited a first layer of Rhodopas D2040 latex, and then a layer of Rhodopas D2040 to which is added an increasing dose of Rhodorsil SP 3301 silicone polyether according to the following plan shown in Table V:

TABLE V

| SAMPLE REFERENCE | NATURE OF TREATING AGENT |
|---|---|
| A | Crude wood |
| B | Latex Rhodopas D2040 RTM Rhodia @ |
| C | Latex D2040 then mixture of LATEX D2040 + 1% SP3301 |
| D | Latex D2040 then mixture of LATEX D2040 + 3% SP3301 |
| E | Latex D2040 then mixture of LATEX D2040 + 5% SP3301 |

These test pieces of wood thus treated were subsequently soiled with various types of soiling, for example dirty motor oil (liquid).

After soiling and drying for 12 hours, the test pieces are simply passed under a stream of water so as to verify the removal of the soiling.

A positive and spectacular effect of the treatment with the latex supplemented with silicone polyether is noted, as shown in the photographs of Figure I.

Even before the washing process, it is noted that the dirty oil does not adhere to the surface treated with the mixtures containing 3% and 5% of silicone polyether (dewetting visible in Figure I).

After passing under water, the soiling is removed much more effectively on the treated test pieces, and completely removed in the case of the test piece treated with a mixture containing 5% of silicone polyether.

We claim:

1. Coating composition, comprising:
an aqueous dispersion of film-forming polymer, and
a sufficient amount of a silicone polyether satisfying formula (I) below:

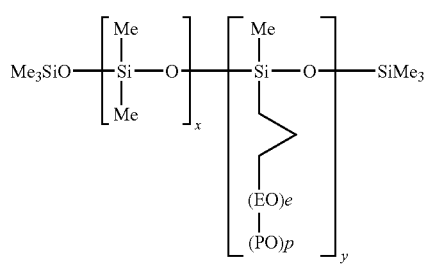

where
EO signifies —O—CH$_2$—CH$_2$—,
PO signifies —O—CH$_2$—CH$_2$—CH$_2$—,
where EO and PO have a terminal Group OR, where R represents a hydrogen atom, or a linear or branched alkyl radical having from 1 to 22 carbon atoms,
x is a number between 5 and 50,
y is a number between 3 and 10,
e is a number between 10 and 30,
p is a number between 0 and 10,
it being understood that:
x/y is less than 10,
e+p is less than 30,
e/p is greater than 1, and
x+y is less than 60, wherein the composition provides for a hydrophilic coating composition with a wetting angle of less than 40° on a hydrophobic support.

2. The composition of claim 1 wherein the silicone polyether is chosen from the silicone polyethers of formula (I) and wherein:
x=9.5, y=3.5, e=11.5 and p=2.5, and R is a hydrogen atom; or
x=14, y=4, e=17 and p=1, and R is a hydrogen atom; or
x=48, y=6, e=15 and p=5, and R is a hydrogen atom.

3. The composition of claim 1 wherein the aqueous dispersion of film-forming polymer comprises at least one water-insoluble polymer obtained by polymerization of monomers chosen from: —vinyl esters, alkyl acrylates and methacrylates having an alkyl group containing from 1 to 10 carbon atoms, vinylaromatic monomers, wherein the monomers maybe copolymerized with one another or with other ethylenically unsaturated monomers copolymerizable therewith so as to form homopolymers, copolymers or terpolymers.

4. The composition of claim 3 wherein the other ethylenically unsaturated monomers are selected from the group consisting of ethylene and other olefins, vinyl esters of branched or unbranched, saturated monocarboxylic acids having from 1 to 12 carbon atoms, esters of unsaturated mono- or dicarboxylic acids having 3 to 6 carbon atoms with alkanols having 1 to 10 carbon atoms, vinylaromatic monomers, vinyl halides, diolefins, (meth)acrylic acid (meth)allyl esters, (meth)allyl esters of maleic acid mono- and diesters, fumaric acid mono- and diesters and itaconic acid mono- and diesters, alkene derivatives of acrylic and methacrylic acid amides and combinations thereof.

5. The composition of claim 4 wherein
the other olefin is isobutene,
the vinyl esters of branched or unbranched, saturated monocarboxylic acids are vinyl propionate, vinyl esters of C$_9$-C$_{11}$ branched acids, vinyl pivalate, vinyl laurate,
the esters of unsaturated mono- or dicarboxylic acids having 3 to 6 carbon atoms with alkanols having 1 to 10 carbon atoms are methyl, ethyl, butyl or ethylhexyl maleates, or methyl, ethyl, butyl or ethylhexyl fumarates,
the vinylaromatic monomers are methylstyrenes or vinyltoluenes,
the vinyl halides are vinyl chloride or vinylidene chloride,
the diolefin is butadiene, and
the methacrylic acid amides is N-methallylmaleimide.

6. The composition of claim 3 wherein the aqueous dispersion of film-forming polymer comprises at least one water-insoluble polymer obtained by polymerization of monomers chosen from alkyl acrylates and methacrylates in which the alkyl group contains from 1 to 10 carbon atoms.

7. The composition of claim 3 wherein
the vinyl esters is vinyl acetate,
the alkyl acrylates and methacrylates are methyl acrylates, ethyl acrylates and methacrylates, n-butyl acrylates and methacrylates, and 2-ethylhexyl acrylates and methacrylates, and wherein
the vinylaromatic monomers is styrene.

8. The composition of claim 1 wherein the sufficient amount of silicone polyether of formula (I) added to the aqueous dispersion of film-forming polymer is between 0.1 and 10% by weight of dry silicone polyether of formula (I) relative to the weight of dry film forming polymer.

9. The composition of claim 8 wherein the sufficient amount of silicone polyether of formula (I) added to the aqueous dispersion of film-forming polymer is between 0.1 and 5% by weight of dry silicone polyether of formula (I) relative to the weight of dry film forming polymer.

10. A process for rendering a hydrophobic support hydrophilic comprising applying a sufficient amount of the coating composition of claim 1 to a surface of the hydrophobic support.

11. The process of claim 10 wherein the hydrophobic support has a contact angle measured by the wetting angle method of greater than 70°.

12. The process of claim 10 wherein the hydrophobic support is a material selected from the group consisting of glass, metals, rigid polypropylene, wood treated with a varnish, and a cement-based material pretreated with a hydrophobic adhesion primer.

13. The process of claim 12 wherein the hydrophobic adhesion primer is a composition of film-foaming polymer as an aqueous dispersion or that is solvent-based.

14. The process of claim 12 wherein the adhesion primer is an aqueous dispersion of film-forming polymer.

15. The process of claim 10, wherein the silicone polyether is chosen from the silicone polyethers of formula (I) and wherein:

x is from 9 to 48;
y is from 3.5 to 6;
e is from 11.5 to 25,
p is from 0.6 to 7, with e+p less than 30.

16. A hydrophobic support having a surface which is coated at least in part with a film resulting from the drying of the composition of claim 1.

17. The hydrophobic support of claim 16, wherein the silicone polyether is chosen from the silicone polyethers of formula (I) and wherein:

x is from 9 to 48;
y is from 3.5 to 6;
e is from 11.5 to 25,
p is from 0.6 to 7, with e+p less than 30.

18. The composition of claim 1 wherein x/y is less than or equal to 8,
e+p is less than or equal to 20,
e/p is greater than or equal to 4, and
x+y is less than 40.

19. The composition of claim 1, wherein the silicone polyether is chosen from the silicone polyethers of formula (I) and wherein:

x is from 9.5 to 48;
y is from 3.5 to 6;
e is from 11.5 to 15,
p is from 2.5 to 5.

* * * * *